United States Patent [19]
Shen et al.

[11] Patent Number: 6,143,923
[45] Date of Patent: Nov. 7, 2000

[54] PROCESS FOR MANUFACTURING 1-HYDROXYALKYLIDENE-1,1-DIPHOSPHONIC ACID (HADP)

[75] Inventors: Shilan Shen, High Bridge, N.J.; Samuel Ellsworth Shull; Scott Brian Harvey, both of Bethlehem, Pa.

[73] Assignee: Lonza Inc., Fair Lawn, N.J.

[21] Appl. No.: 08/725,144

[22] Filed: Oct. 2, 1996

[51] Int. Cl.$^7$ ........................................................ C07F 9/22
[52] U.S. Cl. ................................................................ 562/22
[58] Field of Search ..................................... 568/876, 840; 562/22

[56] References Cited

U.S. PATENT DOCUMENTS

| | | | |
|---|---|---|---|
| 3,366,677 | 1/1968 | Quimby | 260/502.4 |
| 3,959,360 | 5/1976 | Vazopolos . | |
| 4,332,736 | 6/1982 | Starner . | |

*Primary Examiner*—Michael L. Shippen
*Attorney, Agent, or Firm*—Darby & Darby

[57] ABSTRACT

A process for manufacturing 1-hydroxyalkylidene-1,1-diphosphonic Acid (HADP) by introducing phosphorus trihalide ($PX_3$) into a reactor containing aqueous acid of the formula RCOOH at a temperature of 60–200° C. and a pressure of 15–150 psig. Water is added to hydrolyze the intermediate formed to obtain HADP.

23 Claims, No Drawings

PROCESS FOR MANUFACTURING 1-HYDROXYALKYLIDENE-1,1-DIPHOSPHONIC ACID (HADP)

FIELD OF THE INVENTION

This invention relates to a method for manufacturing 1-hydroxyalkylidene-1,1-diphosphonic acid (HADP), particularly 1-hydroxyethylidene 1,1-diphosphonic acid (HEDP).

BACKGROUND OF THE INVENTION

HEDP is commonly used to inhibit corrosion and scale in cooling water systems. It, however, exhibits many properties that are useful in industrial water treatment generally. Thus, it is also used in boiler water treatment, surface cleaning, metal finishing and other industrial operations.

Various processes have been described for producing HEDP. They all, however, suffer from certain disadvantages. The process described in U.S. Pat. No. 3,366,677, for example, uses expensive reagents: phosphorous acid and acetic anhydride.

The process described in U.S. Pat. No. 3,959,360 is difficult to control, and can result in formation of explosive compounds. In that process, $PCl_3$ is first reacted with glacial acetic acid at a temperature of 60–70° C. to form phosphorous acid and acetyl chloride intermediates which slowly react with each other. Gaseous acetyl chloride and $PCl_3$ evolve in this step. Because of this, the process requires strictly controlled feeding of both the $PCl_3$ and acetic acid to maintain the correct hydroxyl balance and to prevent the formation of explosive Lower Oxides Of Phosphorus (LOOP). The next stage involves a long and very difficult to control heating step, in which gaseous acetyl chloride and HCl evolve. Acetic anhydride, which is very expensive, must be added to complete the reaction.

The process of U.S. Pat. No. 4,332,736 improves on that of U.S. Pat. No. 3,959,360, but suffers from serious safety hazards. $PCl_3$ is first fed into a reactor containing glacial acetic acid at a temperature of above 100° C. At this temperature, reaction intermediates (phosphorous acid and acetyl chloride) react with each other almost instantaneously, forming a mass that separates into two phases. The top phase contains primarily acetic acid, with acetyl chloride. The bottom phase contains primarily acetylated HEDP, with phosphorous acid (<5%) and acetic acid. Under atmospheric pressure and a temperature of >100° C., the acetyl chloride is either reacted to form HEDP, or lost overhead and condensed into an acetyl chloride receiver. Because glacial acetic acid is used, each mole of $PCl_3$ generates one mole of HCl, and two moles of excess acetyl chloride which must be separated from the HCl and condensed. Extreme caution must be exercised in handling the acetyl chloride because of its toxicity, volatility, combustibility, and reactivity with water and alkalies. Furthermore, because the reaction temperature is high, HCl gas and unreacted acetyl chloride leave the reactor along with entrained $PCl_3$ and acetic acid. A very large overhead condenser is required to handle this large volume of gases. Also, the entrained $PCl_3$, and phosphorous acid produced by earlier entrained $PCl_3$, can react to generate explosive LOOP. In the final step of the process, intermediates of HEDP are hydrolyzed and vacuum stripped (at 10–50 mmHg and 80–120° C.) to remove acetic acid.

SUMMARY OF THE INVENTION

The present invention provides a process for making 1-hydroxyalkylidene-1,1-diphosphonic acid (HADP) that is economical, safe, and forms little waste product. The process includes the steps of (a) reacting $PX_3$ and aqueous R-COOH at a temperature of between 60° C. and 200° C. and a pressure between 15 and 150 psig, where X is a halogen and R is an alkyl group having from 1 to 18 carbon atoms; and (b) hydrolyzing the product of step (a) with water to form HADP.

DETAILED DESCRIPTION OF THE INVENTION

Following is a description of preferred embodiments of the invention.

In the formula shown in the Summary of the Invention above, R is preferably from 1 to 4 carbon atoms, and most preferably R is $CH_3$, resulting in formation of HEDP. The overall reaction which takes place when carrying out the preferred steps of the invention to produce HEDP is shown below.

$2\ PCl_3 + 5\ H_2O + 2\ CH_3COOH \longrightarrow$

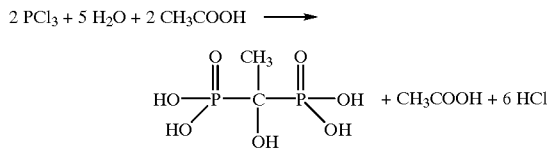

$+ CH_3COOH + 6\ HCl$

While $PCl_3$ is used in the preferred embodiment, it is understood that other halides of the formula $PX_3$ can be substituted.

The process can be started by charging water and acetic acid into a batch reactor. After heating to reaction temperature, $PCl_3$ is metered in over a period of from 1 to 10 hours, preferably continuously over a period of from 3 to 8 hours. The reactants are agitated and the reaction temperature is maintained between 60° C. and 200° C., preferably between 80° C. and 150° C., most preferably between 100° C. and 120° C. The reactor pressure is maintained at between 15 and 150 psig, preferably between 20 and 110 psig, and most preferably between 30 and 80 psig.

Maintaining a high reactor pressure raises the boiling points of acetic acid and $PCl_3$, thereby reducing the amount of gaseous acetic acid and $PCl_3$ that is given off. Formation of LOOP is thereby prevented. The high reactor pressure also retains more acetyl chloride in the reaction mixture, eliminating the need for added acetic anhydride.

Acetyl chloride that is initially formed subsequently reacts to form HEDP. HCl exits the reactor in substantial amounts along with a small amount of the acetyl chloride. A water cooled (less than 30° C.) demister can be used to reduce acetyl chloride entrainment. The acetyl chloride can also be absorbed in a small scrubber, recovered as acetic acid, and then recharged into the next batch reaction. This keeps the HCl scrubber free of acetic acid contamination.

The molar ratio of $PCl_3$:acetic acid:water used is preferably 1.0:1.6–3.3:0.5–1.7, more preferably 1:1.7–2.3:1.0–1.7, and most preferably about 1.0:1.9:1.6. The molar ratio of $PCl_3$:(acetic acid+water, i.e., the total hydroxyl count) should be $1:\geqq 3$. This provides sufficient hydroxyl groups for $PCl_3$ to react with to form $H_3PO_3$. In the absence of sufficient hydroxyl groups, $PCl_3$ reacts with $H_3PO_3$ to form explosive LOOP.

At the end of the $PCl_3$ addition, the reactor mass become turbid and separates into two phases when agitation is stopped. Two phases form because acetylated HEDP is immiscible with acetic acid. After the $PCl_3$ is completely added, the reaction mass is preferably maintained at the reaction temperature for another hour, after which the reactor is slowly vented.

Hydrolysis is carried out by feeding water or steam into the reactor at a temperature of between 60° C. and 200° C., preferably between 110° C. and 140° C., over a period of between 5 minutes and 6 hours. Feeding over a period greater than 30 minutes is preferred, because the hydrolysis reaction is highly exothermic. The preferred mode of feeding is by a subsurface steam sparge. The molar ratio of $PCl_3$ to water is preferably 1:0.8–2.5, more preferably 1:1–2, and most preferably about 1:1.

The excess acetic acid that remains in the reaction mass can then be steam stripped. This is preferably done under a vacuum (100–600 mmHg absolute pressure) at between about 100° C. and 200° C., preferably between about 100° C. and 150° C., most preferably between about 110° C. and 130° C. Steam or hot water is fed at a rate of about 5% and 20%, preferably between about 10% and 15%, of the total reactor charge weight over a period of between about 0.5 and 4 hours, preferably between about 1.5 and 3 hours. Applying a slow steam feed and a moderate vacuum allow reuse of >95% of the acetic acid recovered in the steam stripping process. These parameters also avoid high viscosity and high skin temperature, which degrade the quality of the final product.

This invention is illustrated by the following example, which is intended to exemplify the invention, not to limit its scope.

EXAMPLE 123.1 lbs. of glacial acetic acid and 31.7 lbs. of water were charged into a stirred reaction vessel equipped with a water jacket, pressure control valve (release pressure set at 70 psig), reflux condenser and stripping condenser. The batch was heated to 115° C. When the reactor temperature reached 90° C., $PCl_3$ was pumped at 0.75 lbs./min. to feed 90 lbs of $PCl_3$ below the surface of the reaction mixture over 2.0 hrs. The reactor temperature was maintained at 115±5° C.

The $PCl_3$ pump rate was then lowered to 0.50 lbs./min., to feed 59.7 lbs. of $PCl_3$ into the reactor over an additional 2.0 hrs. The reactor temperature was maintained at 115±5° C. Thus, a total of 149.7 lbs of $PCl_3$ was fed into the reactor over 4.0 hrs.

After the $PCl_3$ addition was completed, the reaction mixture was maintained at 115° C. for an additional hour. The reactor was then sampled for the presence of unreacted phosphorous acid intermediate to determine whether the reaction was complete. When it was determined that the reaction was complete, the pressure was gradually reduced to 5 psi (or lower) by venting over 30 min. When the venting process was complete, the reactor was sealed and 5.7 lbs. of hydrolysis water was fed through a subsurface dip tube at a rate of 0.19 lbs./min. over 30 minutes. The addition rate was controlled to keep the reactor temperature below 130° C. An additional 13.9 lbs. of hydrolysis water was fed over 30 minutes (i.e., a rate of 0.46 lbs./min.), while the reactor temperature was again maintained at 130±5° C.

After water addition was completed, the reactor was maintained at 130° C.±5° C. for an additional hour. Then, maintaining the same temperature, pressure was reduced over 30 minutes to reach a final vacuum of 300 mmHg (abs), the rate being controlled to prevent foaming of the reaction mixture. At 500 mmHg (abs), hot water was pumped into the reactor through a dip tube at a feed rate of 18 lbs./hour.

Distillate was then collected into a first acetic acid receiver for recycling. The distillate was monitored for its concentration of acetic acid. When the acetic acid in the distillate reached a concentration of less than 10 wt. % the distillate was collected in a second receiver. When the acetic acid concentration in the distillate leveled off to below 5 wt. %, the reactor was sampled for percent acetic acid. When residual acetic acid in the reactor was less than 0.3 wt. %, the steam was stopped, the reactor sealed, and nitrogen added to break the vacuum. 56 lbs. of water was pumped through a dip tube and the reactor was cooled down to ~50° C.

We claim:

1. A process for making 1-hydroxyalkylidene-1,1-diphosphonic acid (HADP) consisting essentially of:
    (a) reacting $PX_3$ and aqueous RCOOH at a temperature of between 60° C. and 200° C. and a pressure of between 30 and 150 psig, wherein X is a halogen and R is an alkyl group containing between 1 and 18 carbon atoms, and
    (b) adding water to the product of step (a) to hydrolyze the product and form said HADP.

2. The process of claim 1 wherein R is an alkyl group having from 1 to 4 carbon atoms.

3. The process of claim 1 wherein RCOOH is acetic acid and the product of the process is 1-hydroxyethylidene-1,1-diphosphonic acid.

4. The process of claim 3 wherein the $PX_3$ is $PCl_3$ and the $PCl_3$ is added to the aqueous acetic acid over a period of between about 1 and 10 hours.

5. The process of claim 3 wherein step (a) is conducted at a temperature of between 80° C. and 150° C.

6. The process of claim 3 wherein said pressure in step (a) is between 30 and 110 psig.

7. The process of claim 3 wherein the water is added over a period of between about 5 minutes and 6 hours at a temperature of between 60° C. and 200° C.

8. The process of claim 3 wherein after the completion of step (b) excess acetic acid is removed by steam stripping at a pressure of between about 100 and 600 mmHg (abs) and a temperature of between about 100° C. and 200° C.

9. The process of claim 8 wherein the amount of steam used for stripping is between about 5 and 20 wt % of the amount of the charge to step (a) and step (b), and the time period of the steam stripping is between about 0.5 and 4 hours.

10. A process for making 1-hydroxyethylidene-1,1-diphosphonic acid (HEDP) consisting essentially of:
    (a) reacting $PX_3$ and aqueous acetic acid at a temperature of between, about 100° C. and 120° C., and a pressure between about 30 and 80 psig, wherein X is a halogen and the molar ratio of $PX_3$:acetic acid:water is 1:1.6–3.3:0.5–1.7, and
    (b) adding water to the product of step (a) to hydrolyze the product and form said HEDP, wherein the molar ratio of water added in step (b) to $PX_3$ added in step (a) is 1:0.8–2.5.

11. The process of claim 10 wherein the $PX_3$ is $PCl_3$ and the $PCl_3$ is added to aqueous acetic acid over a period of between about 3 and 8 hours.

12. The process of claim 10 wherein the added water of step (b) is at a temperature of between about 110 and 140° C. and is added over a period of between 0.5 and 3 hours.

13. The process of claim 10 wherein after the completion of step (b) excess acetic acid is removed by steam stripping at a pressure of between about 100 mm and 600 mmHg (abs) and a temperature of between about 100° C. and 150° C.

14. The process of claim 13 wherein the amount of steam used for stripping is 10–15 wt. % of the amount of the charge to steps (a) and (b) and the time period of the steam stripping is between about 1½ and 3 hours.

15. A process for making 1-hydroxyalkylidene-1,1-diphosphonic acid consisting essentially of:
(a) reacting $PCl_3$ and aqueous acetic acid at a temperature of between about 100° C. and 120° C., and a pressure between about 30 and 80 psig, wherein the molar ratio of $PCl_3$:acetic acid:water is about 1:1.7–2.3:1–1.7; and
(b) adding to the product of step (a) and hydrolyzing the product at a temperature of between about 100° C. and 140° C., wherein the molar ratio of water added in step (b) to $PCl_3$ added in step (a) is 1:1–2.

16. The process of claim 15 wherein said molar ratio of $PCl_3$:acetic acid:water is about 1:1.9:1.6.

17. The process of claim 15 wherein said molar ratio of water added in step (b) to $PCl_3$ added in step (a) is about 1:1.

18. The process of claim 15 wherein the $PCl_3$ is added to the aqueous acetic acid over a period of between about 3 and 8 hours.

19. The process of claim 15 wherein the water is added over a period of between 0.5 and 6 hours.

20. The process of claim 15 wherein after the completion of step (b) excess acetic acid is removed by steam stripping at a pressure of between about 100 mm and 600 mmHg (abs) and a temperature of between about 100° C. and 140° C.

21. The process of claim 20 wherein the amount of steam used for stripping is 10–15 wt. % of the amount of the charge to steps (a) and (b) and the time period of steam stripping is between about 1½ and 3 hours.

22. The process of claim 20 wherein the molar ratio of $PCl_3$:(acetic acid plus water) is $1:\geq 3$.

23. The process of claim 15 wherein the $PCl_3$ is fed below the surface of said aqueous acetic acid.

* * * * *